United States Patent
Parker

(10) Patent No.: US 8,175,672 B2
(45) Date of Patent: *May 8, 2012

(54) REUSABLE PULSE OXIMETER PROBE AND DISPOSABLE BANDAGE APPARATII

(75) Inventor: Brent Parker, Murrieta, CA (US)

(73) Assignee: Masimo Corporation, Irvine, CA (US)

( * ) Notice: Subject to any disclaimer, the term of this patent is extended or adjusted under 35 U.S.C. 154(b) by 1311 days.

This patent is subject to a terminal disclaimer.

(21) Appl. No.: 11/774,446

(22) Filed: Jul. 6, 2007

(65) Prior Publication Data

US 2008/0009691 A1    Jan. 10, 2008

Related U.S. Application Data

(63) Continuation of application No. 10/287,795, filed on Nov. 5, 2002, now Pat. No. 7,245,953, which is a continuation-in-part of application No. 09/758,038, filed on Jan. 11, 2001, now Pat. No. 6,684,091, which is a continuation-in-part of application No. 09/417,898, filed on Oct. 14, 1999, now Pat. No. 6,343,224, which is a continuation-in-part of application No. 09/289,647, filed on Apr. 12, 1999, now Pat. No. 6,144,868.

(60) Provisional application No. 60/331,130, filed on Nov. 9, 2001.

(51) Int. Cl.
    *A61B 5/1455*    (2006.01)

(52) U.S. Cl. ........................................ 600/344; 600/310

(58) Field of Classification Search ................. 600/310, 600/322, 323, 340, 344
    See application file for complete search history.

(56) References Cited

U.S. PATENT DOCUMENTS

| 3,463,142 A | 8/1969 | Harte et al. |
| 3,647,299 A | 3/1972 | Lavallee |
| 3,740,570 A | 6/1973 | Kaelin et al. |
| 3,799,672 A | 3/1974 | Vurek |

(Continued)

FOREIGN PATENT DOCUMENTS

AU    745306    5/2000

(Continued)

OTHER PUBLICATIONS

Copending U.S. Appl. No. 12/917,433, filed Nov. 1, 2010, and pending claims.

(Continued)

*Primary Examiner* — Eric Winakur
(74) *Attorney, Agent, or Firm* — Knobbe Martens Olson & Bear LLP

(57) ABSTRACT

An optical probe is usable to determine at least one physiological parameter. A disposable portion of the optical probe comprises a bandage including adhesive on at least a portion of at least one face thereof. The bandage comprises a first modular housing component attached to a surface of the bandage at a first position. The first modular housing component is configured to receive and removably engage a modular probe emitter. The bandage comprises a second modular housing component attached to the surface of the bandage at a second position. The second position is spaced from the first position. The second modular housing component is configured to receive and removably engage a modular probe detector. The bandage is configured with sufficient flexibility that the first modular housing component attached to the bandage surface at the first position is positioned generally opposite the second modular housing component attached to the bandage surface at the second position when the bandage is positioned on an appendage of a patient for sensing a physiological parameter of the patient.

10 Claims, 3 Drawing Sheets

U.S. PATENT DOCUMENTS

| | | | |
|---|---|---|---|
| 4,086,915 A | 5/1978 | Kofsky et al. |
| 4,169,976 A | 10/1979 | Cirri |
| 4,182,977 A | 1/1980 | Stricklin, Jr. |
| 4,308,456 A | 12/1981 | van der Gaag et al. |
| 4,346,590 A | 8/1982 | Brown |
| 4,407,290 A | 10/1983 | Wilber |
| 4,449,821 A | 5/1984 | Lee |
| 4,480,886 A | 11/1984 | Bergamin |
| 4,580,867 A | 4/1986 | Wright et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,700,708 A | 10/1987 | New, Jr. et al. |
| 4,770,179 A | 9/1988 | New, Jr. et al. |
| 4,830,014 A | 5/1989 | Goodman et al. |
| 4,848,901 A | 7/1989 | Hood, Jr. |
| 4,865,038 A | 9/1989 | Rich et al. |
| 4,877,322 A | 10/1989 | Hill |
| 4,913,150 A | 4/1990 | Cheung et al. |
| 4,942,877 A | 7/1990 | Sakai et al. |
| 4,960,128 A | 10/1990 | Gordon et al. |
| 4,964,408 A | 10/1990 | Hink et al. |
| 5,041,187 A | 8/1991 | Hink et al. |
| 5,058,588 A | 10/1991 | Kaestle |
| 5,069,213 A | 12/1991 | Polczynski |
| 5,090,410 A | 2/1992 | Saper et al. |
| 5,094,240 A | 3/1992 | Muz |
| 5,113,862 A | 5/1992 | Mortazavi |
| 5,140,228 A | 8/1992 | Biegel |
| 5,158,323 A | 10/1992 | Yamamoto et al. |
| 5,163,438 A | 11/1992 | Gordon et al. |
| 5,170,786 A | 12/1992 | Thomas et al. |
| 5,209,230 A | 5/1993 | Swedlow et al. |
| 5,226,417 A | 7/1993 | Swedlow et al. |
| 5,246,003 A | 9/1993 | DeLonzor |
| 5,249,576 A | 10/1993 | Goldberger et al. |
| 5,267,562 A | 12/1993 | Ukawa et al. |
| 5,273,041 A | 12/1993 | Richards et al. |
| 5,279,295 A | 1/1994 | Martens et al. |
| 5,287,853 A | 2/1994 | Vester et al. |
| 5,308,919 A | 5/1994 | Minnich |
| 5,337,744 A | 8/1994 | Branigan |
| 5,339,810 A | 8/1994 | Ivers et al. |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| 5,387,122 A | 2/1995 | Goldberger et al. |
| 5,397,247 A | 3/1995 | Aoki et al. |
| D359,546 S | 6/1995 | Savage et al. |
| 5,431,170 A | 7/1995 | Mathews |
| D361,840 S | 8/1995 | Savage et al. |
| 5,437,275 A | 8/1995 | Amundsen et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,460,182 A | 10/1995 | Goodman et al. |
| 5,482,036 A | 1/1996 | Diab et al. |
| 5,490,505 A | 2/1996 | Diab et al. |
| 5,494,043 A | 2/1996 | O'Sullivan et al. |
| 5,507,286 A | 4/1996 | Solenberger |
| 5,515,169 A | 5/1996 | Cargill et al. |
| 5,520,177 A | 5/1996 | Ogawa et al. |
| 5,533,511 A | 7/1996 | Kaspari et al. |
| 5,561,275 A | 10/1996 | Savage et al. |
| 5,562,002 A | 10/1996 | Lalin |
| 5,579,373 A | 11/1996 | Jang |
| 5,590,649 A | 1/1997 | Caro et al. |
| 5,602,924 A | 2/1997 | Durand et al. |
| 5,619,992 A | 4/1997 | Guthrie et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,660,567 A | 8/1997 | Nierlich et al. |
| 5,664,270 A | 9/1997 | Bell et al. |
| 5,673,693 A | 10/1997 | Solenberger |
| 5,678,544 A | 10/1997 | DeLonzor et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,786,592 A | 7/1998 | Hök |
| 5,791,347 A | 8/1998 | Flaherty et al. |
| 5,810,734 A | 9/1998 | Caro et al. |
| 5,817,008 A | 10/1998 | Rafert et al. |
| 5,817,010 A | 10/1998 | Hibl |
| 5,823,950 A | 10/1998 | Diab et al. |
| 5,830,131 A | 11/1998 | Caro et al. |
| 5,833,618 A | 11/1998 | Caro et al. |
| RE36,000 E | 12/1998 | Swedlow et al. |
| 5,860,919 A | 1/1999 | Kiani-Azarbayjany et al. |
| 5,879,373 A | 3/1999 | Roper et al. |
| 5,890,929 A | 4/1999 | Mills et al. |
| 5,904,654 A | 5/1999 | Wohltmann et al. |
| 5,910,108 A | 6/1999 | Solenberger |
| 5,919,133 A | 7/1999 | Taylor et al. |
| 5,919,134 A | 7/1999 | Diab |
| 5,934,925 A | 8/1999 | Tobler et al. |
| 5,940,182 A | 8/1999 | Lepper, Jr. et al. |
| 5,991,648 A | 11/1999 | Levin |
| 5,995,855 A | 11/1999 | Kiani et al. |
| 5,997,343 A | 12/1999 | Mills et al. |
| 5,999,834 A | 12/1999 | Wang et al. |
| 6,002,952 A | 12/1999 | Diab et al. |
| 6,011,986 A | 1/2000 | Diab et al. |
| 6,014,576 A | 1/2000 | Raley |
| 6,027,452 A | 2/2000 | Flaherty et al. |
| 6,036,642 A | 3/2000 | Diab et al. |
| 6,045,509 A | 4/2000 | Caro et al. |
| 6,061,584 A | 5/2000 | Lovejoy et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,308,089 B1 | 10/2001 | von der Ruhr et al. |
| 6,321,000 B1 | 11/2001 | King |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kian |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,381,489 B1 | 4/2002 | Ashibe |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |

| | | |
|---|---|---|
| 6,519,484 B1 | 2/2003 | Lovejoy et al. |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,571,113 B1 | 5/2003 | Fein et al. |
| 6,580,086 B1 | 6/2003 | Schulz et al. |
| 6,580,948 B2 | 6/2003 | Haupert et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,600,940 B1 | 7/2003 | Fein et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,671,532 B1 | 12/2003 | Fudge et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,839,583 B1 | 1/2005 | Lewandowski et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,941,162 B2 | 9/2005 | Fudge et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,706,853 B2 | 4/2010 | Hacker et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |

| | | | | | | |
|---|---|---|---|---|---|---|
| 7,761,128 B2 | 7/2010 | Al-Ali et al. | | JP | 5-200017 | 8/1993 |
| 7,764,982 B2 | 7/2010 | Dalke et al. | | JP | 5275746 | 10/1993 |
| D621,516 S | 8/2010 | Kiani et al. | | JP | 60-34432 | 2/1994 |
| 7,791,155 B2 | 9/2010 | Diab | | JP | 9-504461 | 5/1997 |
| RE41,912 E | 11/2010 | Parker | | JP | 9-506786 | 7/1997 |
| 2001/0029325 A1 | 10/2001 | Parker | | JP | 11-508691 | 7/1999 |
| 2003/0009092 A1 | 1/2003 | Parker | | JP | 3981271 | 7/2007 |
| 2004/0147824 A1 | 7/2004 | Diab et al. | | JP | 4614537 | 10/2010 |
| 2005/0245797 A1 | 11/2005 | Al-Ali et al. | | WO | WO 92/21281 | 10/1992 |
| 2007/0123763 A1 | 5/2007 | Al-Ali et al. | | WO | WO 88/10462 | 12/1998 |
| 2007/0219437 A1 | 9/2007 | Schurman et al. | | WO | WO 99/53831 | 10/1999 |
| 2007/0244378 A1 | 10/2007 | Al-Ali et al. | | WO | WO 00/21433 | 4/2000 |
| 2008/0009691 A1 | 1/2008 | Parker | | WO | WO 00/42911 | 7/2000 |
| 2008/0262324 A1 | 10/2008 | Van Der Voort et al. | | WO | WO 01/03574 | 1/2001 |
| | | | | WO | WO 01/41634 | 6/2001 |
| | FOREIGN PATENT DOCUMENTS | | | WO | WO 02/089664 | 11/2002 |
| AU | 784021 | 5/2006 | | | | |
| CA | 2 346 639 | 4/2000 | | | | |
| CA | 2 366 493 | 11/2002 | | | | |
| EP | 019 478 | 11/1980 | | | | |
| EP | 0 313 238 | 4/1989 | | | | |
| EP | 0 745 348 | 12/1996 | | | | |
| EP | 1 222 894 | 7/2002 | | | | |
| EP | 1 121 049 | 5/2006 | | | | |
| EP | 1 683 478 | 11/2007 | | | | |
| JP | 59-141932 | 8/1984 | | | | |
| JP | 63-192422 | 8/1988 | | | | |
| JP | 2-189132 | 7/1990 | | | | |
| JP | 4-15045 | 1/1992 | | | | |

OTHER PUBLICATIONS

Office Action and translation thereto, Japanese Patent Application No. 2000-575417, mailed Feb. 23, 2010, 6 pages.

PCT International Search Report, Application No. PCT/US2006/046176, App. Date Nov. 29, 2006 in 4 pages.

Copending U.S. Appl. No. 11/404,123, filed Apr. 13, 2006, and pending claims.

Copending U.S. Appl. No. 11/432,798, filed May 11, 2006, and pending claims.

Copending U.S. Appl. No. 12/573,851, filed Oct. 5, 2009, and pending claims.

REUSABLE PULSE OXIMETER PROBE AND DISPOSABLE BANDAGE APPARATII

RELATED APPLICATIONS

This application is a continuation application of Ser. No. 10/287,795 filed Nov. 5, 2002 (now U.S. Pat. No. 7,245,953), which in turn is a continuation-in-part application of Ser. No. 09/758,038 filed Jan. 11, 2001 entitled REUSABLE PULSE OXIMETER PROBE AND DISPOSABLE BANDAGE METHOD (now U.S. Pat. No. 6,684,091), which in turn is a continuation-in-part of application Ser. No. 09/417,898 filed Oct. 14, 1999 (now U.S. Pat. No. 6,343,224), which in turn is a continuation-in-part of Ser. No. 09/289,647 filed Apr. 12, 1999 (now U.S. Pat. No. 6,144,868), and is the subject of provisional application Ser. No. 60/331,130 filed Nov. 9, 2001 and entitled REUSABLE PULSE OXIMETER PROBE AND DISPOSABLE BANDAGE APPARATUS which is incorporated herein by reference.

BACKGROUND OF THE INVENTION

Heretofore the use of pulse oximeter probes has been limited to the use of a costly, reusable probe, which is contaminated by use on a patient, or cheaper, single-use, disposable probes, which in the aggregate, amount to a considerable cost for a healthcare institution. The current applicant in his U.S. Pat. Nos. 6,144,868, 6,321,100 and 6,343,224, and subsequent continuations-in-part, has described a reusable pulse oximeter probe with modular probe housings and a disposable bandage apparatus having at least two modular receptacles thereon. The probe housings can matedly engage said bandage receptacles, and transmit and receive signals through the blood-profused flesh of a patient when said probe and bandage apparatus are resident on a patient. After use on a subject, the disposable bandage apparatus is discarded and the reusable probe can then be reused on another patient in conjunction with a new disposable bandage apparatus.

Although the previously described bandage is very good, there are, in some instances, cases whereby it would be advantageous to offer disposable bandage apparatii having different designs in order for them to work efficiently in a particular situation.

In some cases, female patients will have long fingernails. When a bandage apparatus includes two receptacles with a particular, fixed spacing between the receptacles, it can be difficult, if not impossible, to align the receptacles exactly opposite one another on the finger in order to allow for proper transmission and reception of signals between the light-emitting diode and the photocell detector. In these cases, it could be preferable to offer two bandage apparatii that may be placed independently of one another.

In many cases, it could also be advantageous to have two bandage apparatii connected by a biasing member in order to assure exact alignment of the light-emitting diode and photocell detector on either side of a patient's digit.

Where patients have low peripheral profusion, it may be necessary to affix a probe to an ear or a forehead. Several designs of bandage apparatii are therefore disclosed for these applications.

In addition, when pulse oximetry is used on the forehead, it would be necessary to use a reflectance sensor and corresponding bandage apparatus. Disclosure is therefore made for this type of device as well.

SUMMARY OF THE INVENTION

The following disclosure offers various improvements on a disposable bandage apparatus and a reusable pulse oximeter probe.

What is presently disclosed is at least one bandage apparatus having adhesive on at least a portion of at least one face thereof, and at least one plastic receptacle mounted thereon; and at least one other bandage apparatus having adhesive on at least a portion of at least one face thereof, and having at least one plastic receptacle mounted thereon, wherein said apparatii may be placed on a patient and wherein said at least one receptacle of each at least one bandage apparatus can matedly and removably engage at least one housing of a reusable pulse oximeter probe, said at least one housing incorporating thereon or therein at least one photocell detector, or at least one light-emitting diode.

In addition, the apparatii, as disclosed above, may be connected by a biasing member.

Further, a reusable reflectance probe is disclosed said probe having at least one modular plastic housing said at least one housing having incorporated therein or thereon at least one light-emitting diode, and at least one photocell detector, wherein said probe housing can matedly and removably engage the plastic receptacle of a disposable bandage apparatus, in order to aid in sending and receiving oximetry signals through the blood-profused flesh of a patient.

Further disclosed is a bandage apparatus for use in reflectance oximetry, said bandage apparatus comprising at least one bandage strip having adhesive on at least a port of at least one face thereof, and having at least one receptacle mounted thereon, said receptacle having the capacity to matedly and removably engage the housing of a reusable pulse oximeter probe.

In addition, disclosure is made for a bandage apparatus system for use in reflectance oximetry, said bandage apparatus system comprising at least one bandage strip having adhesive on at least a portion of at least one face thereof, and having at least one plastic receptacle mounted thereon, said receptacle having the capacity to matedly and removably engage the housings of different probes, said probes having been designed to replace a multiplicity of manufacturer's reusable pulse oximeter probes, wherein said probe housings are designed to removably and matedly engage said bandage apparatus.

BRIEF DESCRIPTION OF THE DRAWINGS

The above and other advantages of the invention will become clear when considered with the following specification and accompanying drawings wherein.

DETAILED DESCRIPTION OF THE PREFERRED EMBODIMENTS

The Independent Bandage Apparatii

Figure 1:
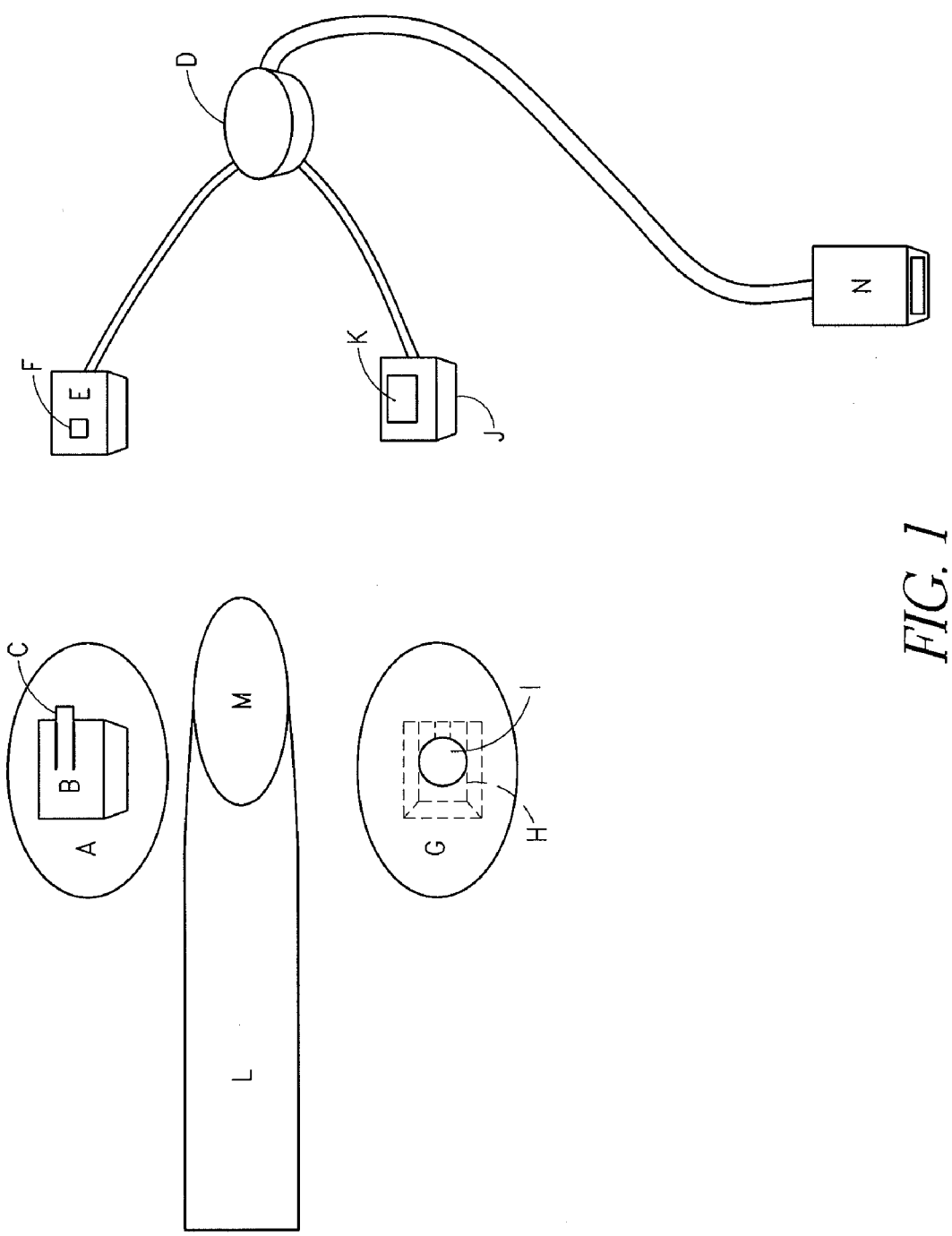
FIG. 1 is an illustration of individual bandage apparatii for more precise placement of a human digit.

The independent bandage apparatii are comprised of a discrete bandage strip, FIG. 1, Item A, which has mounted thereon, a receptacle, FIG. 1, Item B, said receptacle having a locking lever FIG. 1, Item C. The receptacle, FIG. 1, Item B is designed to matedly engage at least one reusable probe housing, FIG. 1, Item E, and to removably retain the probe housing within the bandage receptacle by means of a protrusion on the locking lever which can removably lodge in an indentation, FIG. 1, Item F, in the probe housing. FIG. 1, Item A, represents a view of the superior side of the bandage apparatus and FIG. 1, Item E is a view of the superior side of the reusable probe housing.

A human finger is represented by FIG. 1, Item L, and a fingernail is shown as FIG. 1, Item M.

Figure 2:
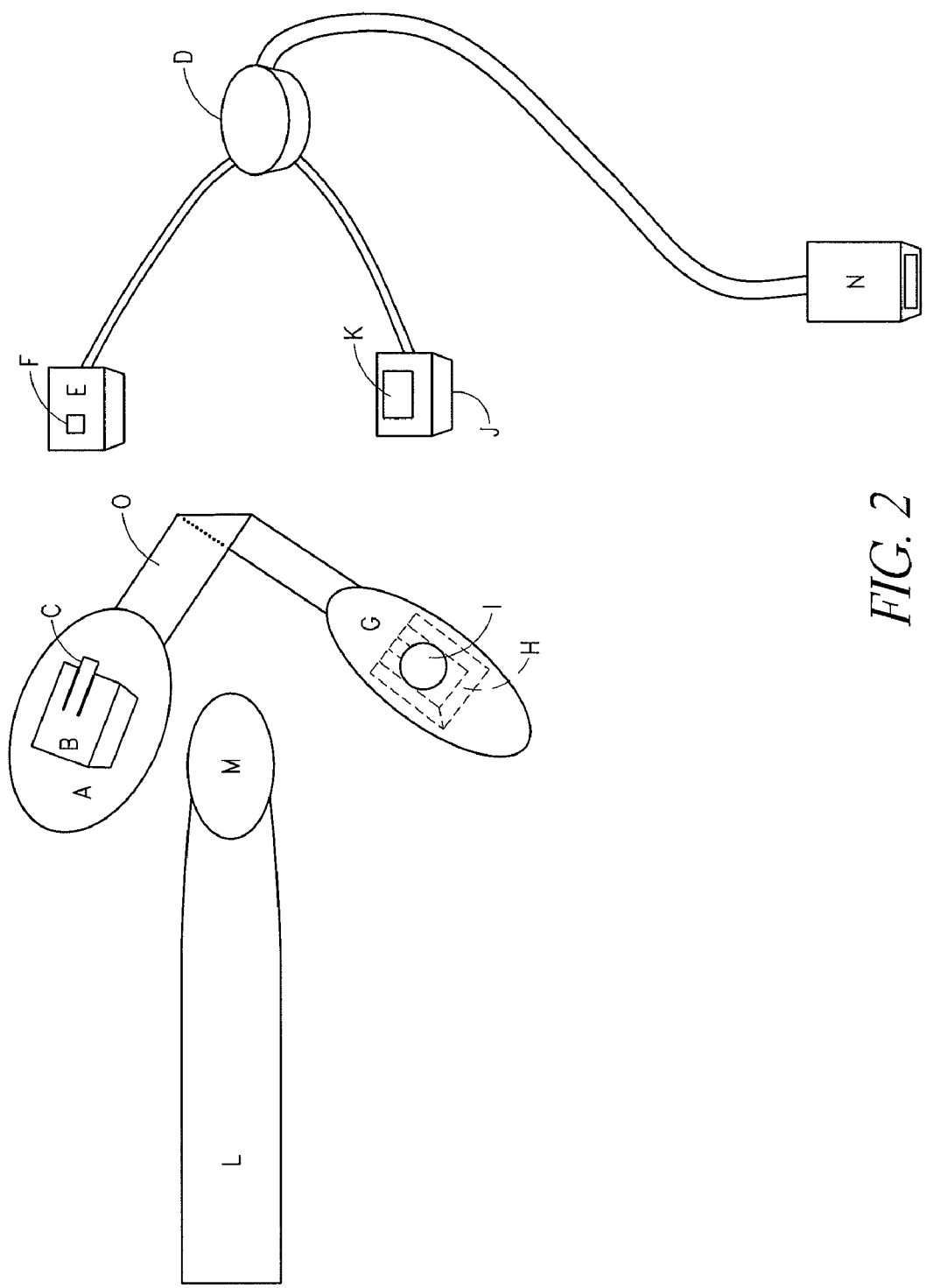
FIG. 2 illustrates individual bandage apparatii connected by a biasing member.

The reusable probe, FIG. 2, Item D, which incorporates housings, FIG. 2, Items E and J, and a connector FIG. 2, Item N, for connecting the probe to the oximeter is not a part of this invention and is shown for illustration purposes only.

The second bandage apparatus is shown in its inferior view as FIG. 2, Item G, and, in this illustration, would be adhered to the underside of the finger. This inferior view illustrates a radiation transparent window, FIG. 2, Item I, which is typical of both bandage apparatii, said radiation transparent windows being designed to align with the radiation transparent windows, FIG. 2, Item K, of the probe housings. FIG. 2, Item J represents an inferior view of the probe housing and illustrates the radiation transparent window that is typical of both probe housings. FIG. 2, Item O represents the biasing member that is designed to incline the two apparatii towards each other, thus giving exact alignment of the radiation transparent windows on either side of the human digit.

Figure 3:
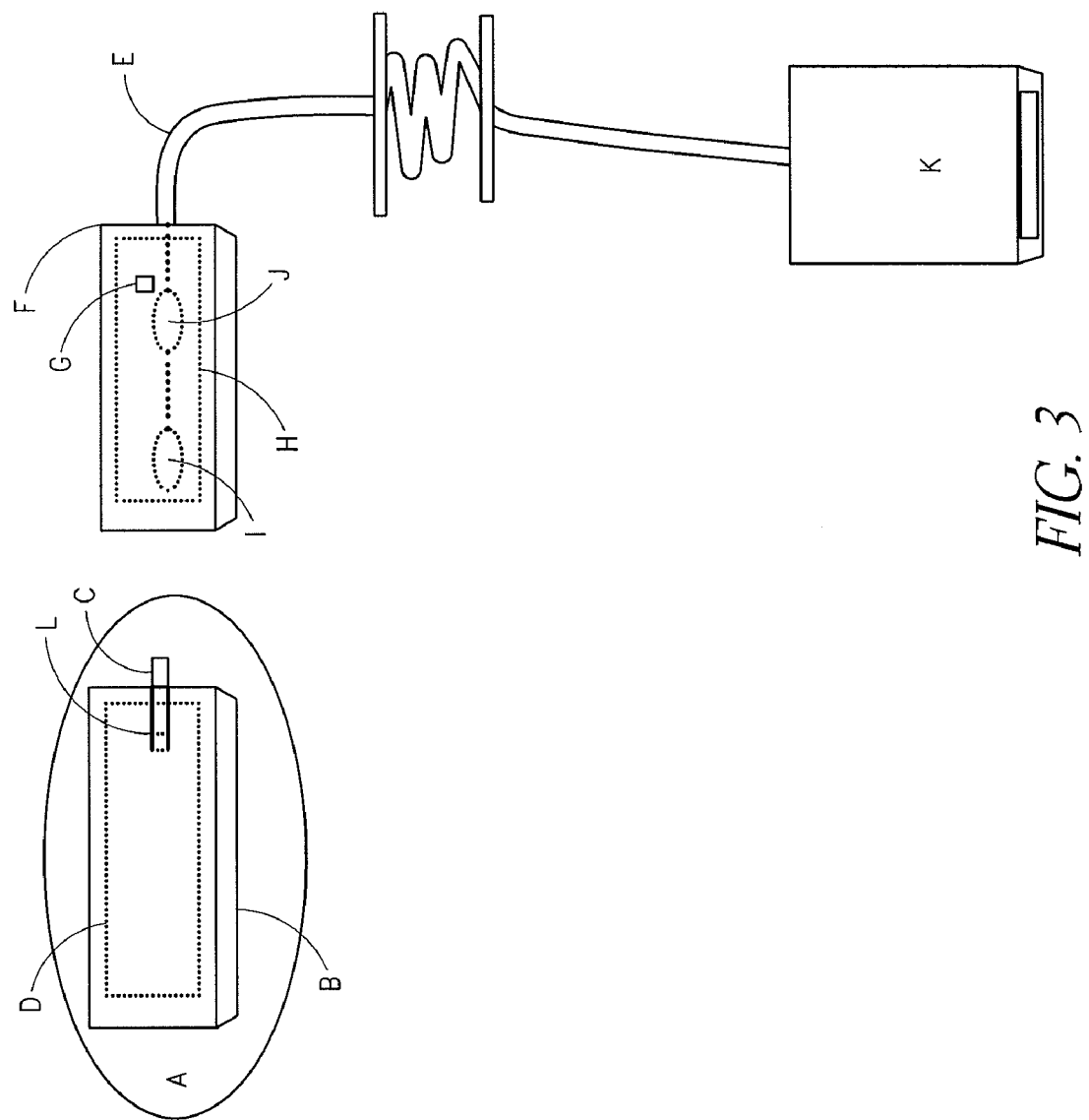
FIG. 3 illustrates a reusable reflectance probe wherein the light-emitting diode and photocell detector of the probe are incorporated into a single probe housing, and it also illustrates a bandage apparatus incorporating one receptacle for matedly and removably engaging a reflectance probe housing having at least one light-emitting diode and at least one photocell detector.

Description of the Reflectance Probe having the Light Emitting Diode and Photocell Detector incorporated into a Plastic Housing and the Bandage Apparatus Designed to Matedly Engage said Probe Housing The reflectance probe having a light emitting diode and photocell detector incorporated into a single plastic housing is shown as FIG. 3, Item F. The probe includes at least one light emitting diode, FIG. 3, Item I, and at least one photocell detector, FIG. 3, Item J, wherein said optical components are incorporated into a plastic housing, FIG. 3, Item F. The housing F also incorporates at least on radiation transparent window, FIG. 3, Item H, which allows for the transmission and/or reception of infrared light through the blood-profased flesh of a patient.

The housing F is designed to matedly and removably engage a bandage receptacle, FIG. 3, Item B, and incorporates a recessed notch, FIG. 3, Item G, for the reception of a protrusion, FIG. 3, Item L, on the locking lever of the bandage receptacle, FIG. 3, Item C, thus removably retaining the probe housing within the bandage receptacle. The bandage apparatus also includes at least one radiation transparent window, FIG. 3, Item A, which is in alignment with the radiation transparent window of the probe housing, FIG. 3, Item H, when said probe housing is resident in said bandage receptacle.

The bandage receptacle also utilizes at least one bandage strip, FIG. 3, Item A, for adhering the bandage apparatus to a patient.

The reflectance probe also incorporates a connector, FIG. 3, Item K, for electrically connecting the probe to an oximeter, said oximeter not being a part of this invention.

Method of Use for the Independent Bandage Apparatii

For use on each individual patient, the independent bandage apparatii are utilized in the following manner:

Firstly, the adhesive backing is removed on one of the apparatii and the apparatus is adhered to the fingernail of a patient. The adhesive backing on the second apparatus is then removed and the apparatus is adhered to the inferior side of the finger in exact alignment with the first apparatus. Once the bandage apparatii are in place, the probe housings can then be inserted into the bandage receptacles in order to monitor the patient.

When there is reason to remove the probe, this is accomplished by lifting up on the locking levers thus releasing the probe housings from the bandage receptacles.

When monitoring is complete, the probe can be removed from the bandage apparatii and can be reused on another patient in conjunction with new bandage apparatii.

Method of Use for the Bandage Apparatii Linked by a Biasing Member

For use on each individual patient, the bandage apparatii incorporating a biasing member is utilized as follows:

Firstly, the adhesive backing is removed on each individual apparatus. Each apparatus is then adhered to the superior and inferior sides of the finger, respectively, with the biasing member protruding off of the distal portion of the finger.

Once the bandage apparatii are in place, the probe housings can then be inserted into the bandage receptacles in order to monitor the patient.

When there is reason to remove the probe, this is accomplished by lifting up on the locking levers thus releasing the probe housings from the bandage receptacles.

When monitoring is complete, the probe can be removed from the bandage apparatii and can be reused on another patient in conjunction with a new bandage apparatus with linked apparatii.

Method of Use for the Reflectance Probe having the Light Emitting Diode and Photocell Detector incorporated into a Plastic Housing and the Bandage Apparatus Designed to Matedly Engage said Probe Housing For use on each individual patient, the reflectance probe and bandage apparatus is used as follows:

Firstly, the adhesive backing is removed from the adhesive strip of the bandage apparatus and it is adhered to the patient. The probe housing is then inserted into the bandage apparatus and the patient can be monitored.

When there is reason to remove the probe, this is accomplished by lifting up on the locking lever thus releasing the probe housing from the bandage receptacle.

When monitoring is complete, the probe can be removed from the bandage apparatus and can be reused on another patient in conjunction with new bandage apparatus.

Advantages of the Present Inventions

Independent bandage apparatii can offer more flexibility to the caregiver for placement on patients with long fingernails or when pulse oximetry is used on the ear or forehead Independent bandage apparatii linked by a biasing member can assure proper alignment between the receptacles of the apparatii and thus the light emitting diode and photocell detector of the probe For reflectance pulse oximetry, it would be an advantage to have a single probe housing incorporating both the photocell detector and light emitting diode of the probe and for removably and matedly attaching said probe housing with a single bandage receptacle. While the invention has been described in relation to preferred embodiments of the invention, it will be appreciated that other embodiments, adaptations and modifications of the invention will be apparent to those skilled in the art.

What is claimed is:

1. A disposable portion of an optical probe usable to determine at least one physiological parameter, the disposable portion comprising a bandage including adhesive on at least a portion of at least one face thereof, the bandage comprising a first modular housing component attached to a surface of the bandage at a first position, the first modular housing component configured to receive and removably engage a modular probe emitter, the bandage comprising a second modular housing component attached to the surface of the bandage at a second position, the second position being spaced from the first position, the second modular housing component configured to receive and removably engage a modular probe detector, the bandage configured with sufficient flexibility that the first modular housing component attached to the bandage surface at the first position is positioned generally opposite the second modular housing component attached to the bandage surface at the second position when the bandage is positioned on an appendage of a patient for sensing a physiological parameter of the patient.

2. The apparatus of claim 1, wherein the bandage is adapted for a single use application in an oximetry system.

3. The apparatus of claim 1, wherein the bandage comprises a radiation transparent window aligned with the first modular housing component.

4. The apparatus of claim 1, wherein the bandage comprises a radiation transparent window aligned with the second modular housing component.

5. The apparatus of claim 1, wherein the bandage defines an opening in the bandage aligned with the first modular housing component.

6. The apparatus of claim 1, wherein the bandage defines an opening in the bandage aligned with the second modular housing component.

7. The apparatus of claim 1, wherein the bandage apparatus comprises an adhesive backing along a majority of at least one face of the bandage.

8. The apparatus of claim 1, wherein the first and second modular housing components each substantially enclose the probe emitter and the probe detector, respectively, when engaged.

9. The apparatus of claim 1, wherein the first and second modular housing components each comprise a locking mechanism for matedly and removably engaging said probe emitter and probe detector, respectively.

10. A method for determining at least one physiological parameter, the method comprising:
    providing a bandage including adhesive on at least a portion of at least one face thereof, the bandage comprising a first modular housing component attached to a surface of the bandage at a first position and the bandage comprising a second modular housing component attached to the surface of the bandage at a second position, the second position being spaced from the first position;
    positioning the bandage on an appendage of a patient such that the first modular housing component attached to the bandage surface at the first position is positioned generally opposite the second modular housing component attached to the bandage surface at the second position on opposite sides of the appendage;
    engaging a modular probe emitter with the first modular housing component;
    engaging a modular probe detector with the second modular housing component;
    sensing a physiological parameter of the patient;
    disengaging a modular probe emitter from the first modular housing component;
    disengaging a modular probe detector from the second modular housing component; and
    disposing of the bandage.

\* \* \* \* \*